(12) United States Patent  
Abdallah et al.

(10) Patent No.: US 8,933,254 B2  
(45) Date of Patent: Jan. 13, 2015

(54) PROCESS FOR MAKING ETHYLENE OXIDE

(75) Inventors: Radwan Abdallah, Ludwigshafen (DE); Torsten Mäurer, Lambsheim (DE); Tobias Rosendahl, Mannheim (DE); Frank Rosowski, Mannheim (DE); Gerhard Theis, Maxdorf (DE); Terry Mazanec, Solon, OH (US); Soumitra Deshmukh, Dublin, OH (US); Laura J. Silva, Dublin, OH (US)

(73) Assignee: BASF SE, Ludwigshafen (DE)

( * ) Notice: Subject to any disclaimer, the term of this patent is extended or adjusted under 35 U.S.C. 154(b) by 872 days.

(21) Appl. No.: 13/003,995

(22) PCT Filed: Jul. 13, 2009

(86) PCT No.: PCT/EP2009/058883  
§ 371 (c)(1),  
(2), (4) Date: Jan. 13, 2011

(87) PCT Pub. No.: WO2010/007011  
PCT Pub. Date: Jan. 21, 2010

(65) Prior Publication Data  
US 2011/0118487 A1 May 19, 2011

Related U.S. Application Data

(60) Provisional application No. 61/080,347, filed on Jul. 14, 2008, provisional application No. 61/109,006, filed on Oct. 28, 2008.

(51) Int. Cl.  
*C07D 301/03* (2006.01)  
*C07D 301/10* (2006.01)

(52) U.S. Cl.  
CPC .................................. *C07D 301/10* (2013.01)

USPC ............................. 549/536; 549/534; 549/537

(58) Field of Classification Search  
CPC ................ C07D 301/10; B01J 19/0093; B01J 2219/00781; B01J 23/68  
USPC .................. 502/243, 344; 549/536, 534, 537; 422/211, 603  
See application file for complete search history.

(56) References Cited

U.S. PATENT DOCUMENTS 3,882,049 A   5/1975   Bertolacini et al.  
3,972,837 A   8/1976   Acres et al.  
(Continued)

FOREIGN PATENT DOCUMENTS

BE   896248      9/1983  
BE   896248 A1   9/1983  
(Continued)

OTHER PUBLICATIONS

U.S. Appl. No. 12/967,337, Altwasser et al.  
(Continued)

*Primary Examiner* — T. Victor Oh  
(74) *Attorney, Agent, or Firm* — Drinker Biddle & Reath LLP

(57) ABSTRACT

This invention relates to a process, comprising reacting ethylene and oxygen or a source of oxygen in the presence of a catalyst in a reactor to form a product comprising ethylene oxide, wherein the catalyst contains silver or silver compound and a support and the catalyst is in the form of particulate solids having a mean particle diameter from 1 to 1000 μm and wherein the molar ratio of oxygen to ethylene is from 1:4 to 10:1.

9 Claims, 5 Drawing Sheets

(56) References Cited

U.S. PATENT DOCUMENTS

| | | |
|---|---|---|
| 4,089,810 A | 5/1978 | Diwell et al. |
| 4,096,095 A | 6/1978 | Cairns |
| 4,289,652 A | 9/1981 | Hunter et al. |
| 4,524,236 A | 6/1985 | McCain |
| 4,760,042 A | 7/1988 | Armstrong |
| 4,908,343 A | 3/1990 | Bhasin |
| 5,145,824 A | 9/1992 | Buffum et al. |
| 5,248,251 A | 9/1993 | Dalla Betta et al. |
| 5,504,053 A | 4/1996 | Chou et al. |
| 5,597,773 A | 1/1997 | Evans et al. |
| 5,703,253 A | 12/1997 | Evans et al. |
| 5,705,661 A | 1/1998 | Iwakura et al. |
| 6,040,266 A | 3/2000 | Fay, III et al. |
| 6,153,556 A | 11/2000 | Shima et al. |
| 6,372,925 B1* | 4/2002 | Evans et al. .......... 549/536 |
| 6,409,072 B1 | 6/2002 | Breuer et al. |
| 6,440,895 B1 | 8/2002 | Tonkovich et al. |
| 6,713,036 B1 | 3/2004 | Vanden et al. |
| 6,762,311 B2 | 7/2004 | Rizkalla et al. |
| 7,294,734 B2 | 11/2007 | Brophy et al. |
| 8,025,846 B2 | 9/2011 | Cremer et al. |
| 2002/0028164 A1 | 3/2002 | Schutte et al. |
| 2002/0192118 A1 | 12/2002 | Zech et al. |
| 2003/0007904 A1 | 1/2003 | Tonkovich et al. |
| 2004/0034111 A1 | 2/2004 | Tonkovich et al. |
| 2004/188326 A1 | 9/2004 | Tonkovich et al. |
| 2004/0229752 A1 | 11/2004 | Long et al. |
| 2005/0163701 A1 | 7/2005 | Tonkovich et al. |
| 2005/0165121 A1 | 7/2005 | Wang et al. |
| 2005/0176832 A1 | 8/2005 | Tonkovich et al. |
| 2006/0036106 A1 | 2/2006 | Mazanec et al. |
| 2007/0197801 A1 | 8/2007 | Bolk et al. |
| 2007/0197808 A1 | 8/2007 | Bolk et al. |
| 2008/0031788 A1 | 2/2008 | Brophy et al. |
| 2008/0081920 A1 | 4/2008 | Gueckel |
| 2008/0177105 A1 | 7/2008 | Raichle et al. |
| 2008/0214863 A1 | 9/2008 | Cremer et al. |
| 2008/0312477 A1 | 12/2008 | Raichle et al. |
| 2010/0029955 A1 | 2/2010 | Wilmer et al. |
| 2010/0069659 A1 | 3/2010 | Raichle et al. |
| 2010/0069660 A1 | 3/2010 | Raichle et al. |
| 2010/0226841 A1 | 9/2010 | Thiele |
| 2011/0009653 A1 | 1/2011 | Mazaneset et al. |
| 2011/0028740 A1 | 2/2011 | Dobner et al. |
| 2011/0034707 A1 | 2/2011 | Wilmer et al. |
| 2011/0094381 A1 | 4/2011 | Lichtfers |
| 2011/0124885 A1 | 5/2011 | Altwasser et al. |
| 2011/0135549 A1 | 6/2011 | Lichtfers |

FOREIGN PATENT DOCUMENTS

| | | |
|---|---|---|
| CA | 2247662 | 9/1998 |
| CA | 2571986 | 6/2007 |
| DE | 246257 | 6/1987 |
| DE | 3926466 | 2/1991 |
| EP | 0 266 015 | 5/1988 |
| EP | 0266015 A1 | 5/1988 |
| EP | 0 327 356 | 8/1989 |
| EP | 0327356 A1 | 8/1989 |
| EP | 357292 A1 | 3/1990 |
| EP | 0 357 292 | 7/1990 |
| EP | 0 425 020 | 10/1990 |
| EP | 0425020 A1 | 5/1991 |
| EP | 0496470 A1 | 7/1992 |
| EP | 0 532 325 | 3/1993 |
| EP | 0 496 470 | 9/1994 |
| EP | 0 625 370 | 11/1994 |
| EP | 0625370 A1 | 11/1994 |
| EP | 0 716 884 | 12/1995 |
| EP | 0716884 A2 | 6/1996 |
| EP | 0 764 464 | 3/1997 |
| EP | 0764464 A2 | 3/1997 |
| EP | 1 002 575 | 5/2000 |
| EP | 1002575 A2 | 5/2000 |
| EP | 1292587 A2 | 3/2003 |
| EP | 1 312 411 | 5/2003 |
| EP | 1 292 587 | 10/2006 |
| EP | 1 102 628 | 11/2006 |
| EP | 1 927 398 | 6/2008 |
| EP | 1927398 A1 | 6/2008 |
| EP | 2062641 A1 | 5/2009 |
| FR | 2 895 278 | 6/2007 |
| GB | 1 531 134 | 11/1978 |
| GB | 2 077 136 | 12/1981 |
| GB | 2 433 501 | 6/2007 |
| GB | 2 433 503 | 6/2007 |
| WO | WO 94/21372 | 9/1994 |
| WO | WO 95/17957 | 7/1995 |
| WO | WO-95/17957 A1 | 7/1995 |
| WO | WO 96/23585 | 8/1996 |
| WO | WO-96/23585 A1 | 8/1996 |
| WO | WO 97/00442 | 1/1997 |
| WO | WO 98/28073 | 7/1998 |
| WO | WO 98/37457 | 8/1998 |
| WO | WO 98/38147 | 9/1998 |
| WO | WO 99/16542 | 4/1999 |
| WO | WO 00/06301 | 2/2000 |
| WO | WO 01/83105 | 11/2001 |
| WO | WO-01/83105 A1 | 11/2001 |
| WO | WO 01/96324 | 12/2001 |
| WO | WO-01/96324 A2 | 12/2001 |
| WO | WO 02/18042 | 3/2002 |
| WO | WO 03/006149 | 1/2003 |
| WO | WO 03/044003 | 5/2003 |
| WO | WO-03/044003 A1 | 5/2003 |
| WO | WO 03/072246 | 9/2003 |
| WO | WO-03/072246 A2 | 9/2003 |
| WO | WO 03/106386 | 12/2003 |
| WO | WO 2004/002971 | 1/2004 |
| WO | WO 2004/030813 | 4/2004 |
| WO | WO-2004/030813 A1 | 4/2004 |
| WO | WO 2004/037418 | 6/2004 |
| WO | WO 2004/091771 | 10/2004 |
| WO | WO 2004/099113 | 11/2004 |
| WO | WO-2004/099113 A1 | 11/2004 |
| WO | WO 2004/101141 | 11/2004 |
| WO | WO 2004/103549 | 12/2004 |
| WO | WO 2005/003025 | 1/2005 |
| WO | WO 2006/020709 | 2/2006 |
| WO | WO-2006/020709 A1 | 2/2006 |
| WO | WO 2006/055609 | 5/2006 |
| WO | WO 2006/133183 | 12/2006 |
| WO | WO-2006/133183 A2 | 12/2006 |
| WO | WO 2007/071737 | 6/2007 |
| WO | WO-2007/071739 A1 | 6/2007 |
| WO | WO 2007/071741 | 6/2007 |
| WO | WO 2007/071744 | 6/2007 |
| WO | WO 2007/076390 | 7/2007 |
| WO | WO 2007/076392 | 7/2007 |
| WO | WO 2007/076393 | 7/2007 |
| WO | WO 2007/076394 | 7/2007 |
| WO | WO 2007/076395 | 7/2007 |
| WO | WO 2007/076397 | 7/2007 |
| WO | WO 2007/076400 | 7/2007 |
| WO | WO 2007/076402 | 7/2007 |
| WO | WO 2007/076404 | 7/2007 |
| WO | WO 2007/076406 | 7/2007 |
| WO | WO 2007/111997 | 10/2007 |
| WO | WO 2007/112866 | 10/2007 |
| WO | WO 2007/122090 | 11/2007 |
| WO | WO 2007/123932 | 11/2007 |
| WO | WO-2007/123932 A2 | 11/2007 |
| WO | WO-2008/030467 A2 | 3/2008 |
| WO | WO 2008/032797 | 3/2008 |
| WO | WO-2008/032797 A1 | 3/2008 |
| WO | WO 2010/007011 | 1/2010 |
| WO | WO 2010/009021 | 1/2010 |
| WO | WO 2010/133461 | 11/2010 |

(56) References Cited

FOREIGN PATENT DOCUMENTS

WO  WO 2010/142714  12/2010
ZA  855317  7/1985

OTHER PUBLICATIONS

U.S. Appl. No. 13/021,242, Ewald et al.
U.S. Appl. No. 13/052,140, Altwasser et al.
U.S. Appl. No. 13/321,129, filed Nov. 17, 2011, Abdallah et al.
Int'l Preliminary Report on Patentability of the Int'l Searching Authority: App. No. PCT/EP2009/050342, issued Jan. 14, 2011.
Int'l Search Report, App. No. PCT/US2009/050342, mailed Feb. 25, 2010.
Kesienbaum et al., "Silver-Catalyzed Oxidation of Ethylene Oxide in a Microreaction System", Industrial & Eng. Chem. Research. American Chem. Society, US, vol. 41—Jan. 1, 2002, pp. 710-719.
Ullmann's Encycl. of Industrial Chem: "Microreactors", vol. 22, Jan. 1, 2003, pp. 1-29.
Iglesia: "Design, synthesis, and use of cobalt-based Fischer-Tropsch synthesis catalyst": Applied Catalysis A.: General 161 (1997): pp. 59-78.
Cybulski et al.: "Monoliths in Heterogeneous Catalysis", Catal. Rev.—Sci. Eng. 36(2), 179-270 (1994).
Bennett et al.: "Microchannel cooled heatsinks for high average power laser diode arrays", SPIE, vol. 1865; 1993; pp. 144-153.
Kursawe et al.: "Selective Reractions in Microchannel Reactors"; Microreaction Technology: $3^{rd}$ Int'l conference on Microreaction Technology, Proceedings of IMRET 3, 1999, pp. 213-223.
Kestenbaum et al., "Silver-Catalyzed Oxidation of Ethylene Oxide in a Microreaction System", Industrial & Eng. Chem. Research, American Chem. Society, US, vol. 41—Jan. 1, 2002, pp. 710-719.
U.S. Appl. No. 61/080,347, filed Jul. 14, 2008.
U.S. Appl. No. 61/109,006, filed Oct. 28, 2008.
U.S. Appl. No. 13/109,945, filed May 17, 2011, Thiele et al.

* cited by examiner

PROCESS FOR MAKING ETHYLENE OXIDE

CROSS-REFERENCE TO RELATED APPLICATIONS

This application is a national stage application (under 35 U.S.C. §371) of PCT/EP2009/058883, filed Jul. 13, 2009, which claims benefit of U.S. application 61/080,347, filed Jul. 14, 2008 and U.S. Provisional Application 61/109,006, filed Oct. 28, 2008. The contents of each of these applications are incorporated herein by reference in their entireties.

FIELD OF THE INVENTION

This invention relates to a process, comprising reacting ethylene and oxygen or a source of oxygen in the presence of a catalyst in a reactor to form a product comprising ethylene oxide, wherein the catalyst contains silver or silver compound and a support and the catalyst is in the form of particulate solids having a mean particle diameter from 1 to 1000 μm and wherein the molar ratio of oxygen to ethylene is from 1:4 to 10:1.

BACKGROUND

Ethylene oxide is typically produced by the oxidation of ethylene with oxygen in the presence of a catalyst. The reaction is exothermic.

A problem with ethylene oxide production relates to the fact that as a production run progresses, the catalyst gradually deactivates. This may be compensated for by allowing the catalyst temperature to increase. This will prolong the production run, but at some point an end of the run (EOR) temperature for the production run will occur. This will occur when the rate of production of ethylene oxide declines to a point at which the run is no longer economical. For the production of ethylene oxide the EOR temperature is typically about 270 to 280° C. The start-of-run (SOR) temperature is usually about 220 to 240° C. Therefore, the deactivation of the catalyst can be compensated by a gradual temperature increase. The change of catalysts will require a shut down of the process. These shut downs are time consuming and costly.

During the lifetime of a catalyst in a state of the art process of making ethylene oxide usually 2 to 4 kilotons of ethylene oxide are produced per cubic meter of catalyst, typically under a work rate of usually 150 to 250 kilograms of produced ethylene oxide per cubic meter per catalyst per hour. The selectivity is depending on the catalyst type, it is usually about 75 to 82% for a high activity catalyst and 82 to 89% for a high selectivity catalyst.

The process of making ethylene oxide is typically conducted in a fixed bed reactor using catalysts in the form of extrudes having dimensions of 3-12 mm as described in US 2008/0081920 and EP 266 015. Usually high selective catalysts are used with a promoting amount of rhenium of about 0.01 to 15 mmol/kg catalyst (see EP 266 015).

Most recently the process of making ethylene oxide using a microchannel reactor is studied (see WO 2008/030467, WO 2006/020709, WO 2007/071739 and US 2008/0031788). Typically, the catalyst is used in the form of a thin coat on the reactor wall. It is well known that wall coated microchannel reactors offer a good heat removal and allow to obtain a stable catalyst operation. However, the catalyst volume ratio to the reactor volume is too low to offer the world scale production capacity of about 150-250 kt/a. Thus, no commercial process is yet available.

BRIEF SUMMARY

Thus, the task of the present invention was to find a process condition were higher productivity per catalyst volume and/or higher selectivity could be reached. In addition, the increase of the lifetime of such epoxidation catalysts by reducing the SOR temperature of the process of making ethylene oxide in view of the state of the art will have a direct positive effect on the average cumulative selectivity. Another task of the present invention was to increase the selectivity and/or productivity of high active catalysts.

With the present invention it is possible to achieve higher work rates for a catalyst and/or a longer catalytic life. In addition, it is possible to use high active catalyst obtaining a high selectivity. All of this contributes to higher levels of productivity. For example, it is estimated that the catalyst life for the ethylene oxide process conducted in a state of the art process using certain catalysts, may be about 7000 hours, while with the inventive process employing catalysts containing silver or silver compound and a support, being in the form of particulate solids and having a mean particle diameter from 1 to 1000 μm and wherein the ratio of oxygen to ethylene is from 1:4 to 10:1, the catalyst life may be about 25,000 hours or longer.

DETAILED DESCRIPTION OF THE PREFERRED EMBODIMENTS

Figure 1:
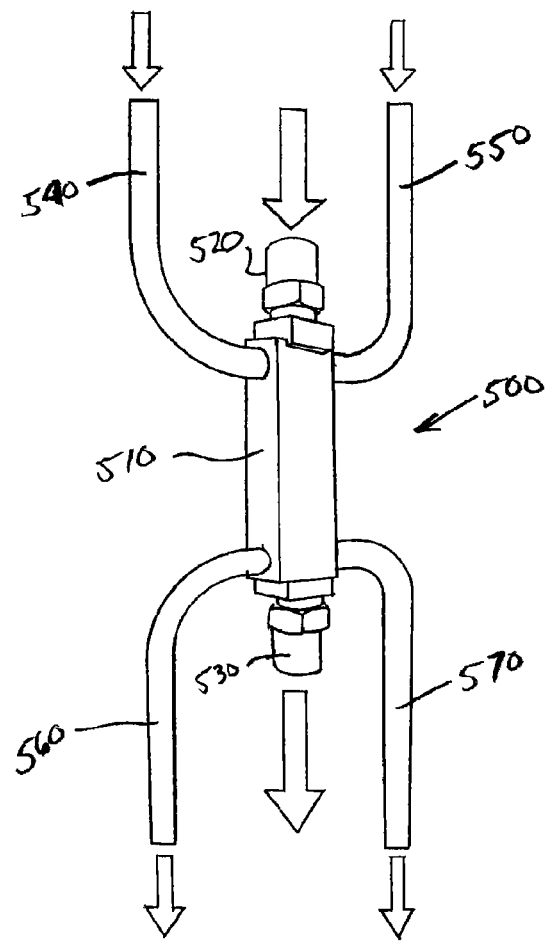
FIG. 1 shows a microchannel reactor that may be used in connection with a process for converting ethylene and oxygen to ethylene oxide.

This invention relates to a process, comprising reacting ethylene and oxygen or a source of oxygen in the presence of a catalyst in a reactor to form a product comprising ethylene oxide, wherein the catalyst contains silver or silver oxide and a support and the catalyst is in the form of particulate solids having a mean particle diameter from 1 to 1000 μm and wherein the molar ratio of oxygen to ethylene is from 1:4 to 10:1.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural. All combinations specified in the claims may be combined in any manner.

Reference to "channel" may include a whole reactor as fixed bed reactor, fluidized bed reactor or microchannel reactor(s) or may include some channels of a fixed bed reactor or microchannel reactor or single channels of a fixed bed reactor or microchannel reactor.

The term "microchannel reactor" refers to an apparatus comprising one or more process microchannels wherein a reaction process is conducted. When two or more process microchannels are used, the process microchannels may be operated in parallel. The microchannel reactor may include a header or manifold assembly for providing for the flow of fluid into the one or more process microchannels, and a footer or manifold assembly providing for the flow of fluid out of the one or more process microchannels. The microchannel reactor may further comprise one or more heat exchange channels adjacent to and/or in thermal contact with the one or more process microchannels. The heat exchange channels may provide heating and/or cooling for the fluids in the process microchannels. The heat exchange channels may be microchannels. The microchannel reactor may include a header or manifold assembly for providing for the flow of heat exchange fluid into the heat exchange channels, and a footer or manifold assembly providing for the flow of heat exchange fluid out of the heat exchange channels.

The term "process microchannel" refers to a microchannel wherein a process is conducted.

The term "microchannel" refers to a channel having at least one internal dimension of height or width of up to about 10 mm, and in one embodiment up to about 5 mm, and in one embodiment up to about 2 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. The length of the microchannel may be at least about two times the height or width, and in one embodiment at least about five times the height or width, and in one embodiment at least about ten times the height or width. The height or width may be referred to as the gap between opposed internal walls of the microchannel. The internal height or width of the microchannel may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other internal dimension of height or width may be of any dimension, for example, up to about 3 meters, and in one embodiment about 0.01 to about 3 meters, and in one embodiment about 0.1 to about 3 meters. The length of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The microchannel may have a cross section having any shape, for example, a square, rectangle, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "catalyst" includes the support and the active composition as well as an inter-facial or buffer layer if present.

The term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnation solution.

The term "volume" with respect to volume within a reactor includes all volume in the reactor a process fluid may flow through or flow by.

The term "fluid" refers to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

The terms "gas" and "vapor" have the same meaning and are sometimes used inter-changeably.

The term "residence time" or "average residence time" refers to the internal volume of a space within a channel occupied by a fluid flowing in the space divided by the average volumetric flow rate for the fluid flowing in the space at the temperature and pressure being used.

The term "contact time" refers to the residence time at normal temperature and pressure conditions.

The term "GHSV" or "gas hourly space velocity" refers to the volume of total gas feed per hour per volume of catalyst.

The terms "upstream" and "downstream" refer to positions within a channel or in a process or process flow sheet that is relative to the direction of flow of a fluid in the channel or process or process flow sheet. For example, a position within a channel or a process or process flow sheet not yet reached by a portion of a fluid stream flowing toward that position would be downstream of that portion of the fluid stream. A position within the channel or a process or process flow sheet already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The term "process fluid" refers to reactants, products, diluents and/or other fluid that enters, flows in and/or flows out of a reactor.

The term "reactants" refers to ethylene and/or oxygen or a source of oxygen when used with reference to the inventive process for converting ethylene and oxygen or a source of oxygen to ethylene oxide.

The term "reaction zone" refers to the space within a reactor wherein a chemical reaction occurs or wherein a chemical conversion of at least one species occurs. The reaction zone may contain one or more catalysts.

The term "cubic meter of catalyst" refers to the volume of the catalytically active portion of a catalyst. For a bed of particulate solids the term "cubic meter of catalyst" may refer to the volume of the space in which the active catalyst is loaded.

The term "heat exchange channel" refers to a channel having a heat exchange fluid in it that gives off heat and/or absorbs heat. The heat exchange channel may absorb heat from or give off heat to an adjacent channel and/or one or more channels in thermal contact with the heat exchange channel. The heat exchange channel may absorb heat from or give off heat to channels that are adjacent to each other but not adjacent to the heat exchange channel. In one embodiment, one, two, three or more channels may be adjacent to each other and positioned between two heat exchange channels.

The term "heat transfer wall" refers to a common wall between a process channel and an adjacent heat exchange channel where heat is transferred from one channel to the other through the common wall.

The term "heat exchange fluid" refers to a fluid that may give off heat and/or absorb heat.

The term "heat exchange medium" refers to a substance or device that absorbs heat or gives off heat and may be used to cool or heat another substance or device. Another substance or device may be, for example, a channel that is adjacent to or in thermal contact with the heat exchange medium. An example of a heat exchange medium would be a heat exchange fluid in a heat exchange channel.

The term "conversion of reactant" refers to the reactant mole change between a fluid flowing into a reactor and a fluid flowing out of the reactor divided by the moles of reactant in the fluid flowing into the reactor.

The term "yield" is used herein to refer to the number of moles of product flowing out of a reactor divided by the number of moles of a reactant flowing into the reactor.

The term "cycle" is used herein to refer to a single pass of the reactants through a reactor.

The term "conversion of ethylene" refers to the number of moles of carbon observed in the reactor exit stream as ethylene oxide and carbon dioxide divided by the total number of moles of carbon exiting the reactor as ethylene, ethylene oxide and carbon dioxide.

The term "conversion of oxygen" refers to the number of moles of oxygen observed in the reactor exit stream as ethylene oxide and carbon dioxide divided by the total number of moles of oxygen exiting the reactor as oxygen, ethylene oxide and carbon dioxide.

The concentration of a reactant "on a whole feed basis" refers to the total amount of the reactant (e.g., oxygen) flowing into a reactor. This would include reactant flowing into the front entrance of a reactor as well as reactant flowing into the reactor through openings in its sidewall downstream from the entrance. The downstream addition of a reactant may be referred to as a "staged addition" of the reactant.

The term "selectivity to ethylene oxide" ($S_{EO}$) refers to the extent of production of ethylene oxide from ethylene. Selectivity to ethylene oxide may be calculated for the oxidation of ethylene to ethylene oxide with carbon dioxide as an unwanted side product using the reaction stoichiometry wherein one mole of ethylene consumes one-half mole of oxygen for the formation of ethylene oxide and three moles of oxygen for the formation of carbon dioxide. Mathematically, in the case of a balanced system, this may be expressed as:

$$S_{EO} = \frac{6}{5} - \frac{2}{5}\frac{\dot{n}_O X_O}{\dot{n}_E X_E} \text{ where } \frac{\dot{n}_O}{\dot{n}_E}$$

is the ratio of the molar feed rates of oxygen and ethylene i.e., a ratio of their feed concentrations. $X_E$ and $X_O$ denote the conversion of ethylene and the conversion of oxygen, respectively.

The term "average ethylene oxide selectivity" ($S_{EO}$ average) refers to the percentage of ethylene oxide produced from ethylene over a catalyst life.

The term "catalyst productivity" refers to the cumulative amount of ethylene oxide produced for a catalyst, measured in the amount (e.g., kilotons (kt)) of ethylene oxide produced per cubic meter of catalyst ($kt_{EO}/m^3_{cat}$).

The term "quench" refers to a process by which a chemical reaction is terminated using a rapid reduction in temperature of the reaction mixture, a rapid introduction of a reactant or non-reactant fluid into the reaction mixture, or flowing the reaction mixture through a restricted opening or passageway having a dimension at or below the quench diameter.

The term "quench diameter" refers to the internal dimension (e.g., height, width, and diameter) of an opening or passageway for a reaction mixture to flow through below which the reaction terminates.

The term "start-of-run" (SOR) refers to the point in time during a production run at which the process begins to produce ethylene oxide at a rate of at least about 250 kilograms per cubic meter of catalyst per hour ($kg/m^3_{cat}/hr$). The start-of-run temperature may be in the range from about 150° C. to about 250° C., and in one embodiment in the range from about 150° C. to about 240° C., and in one embodiment in the range from about 150° C. to about 230° C., and in one embodiment in the range from about 150° C. to about 220° C., and in one embodiment in the range from about 150° C. to about 210° C., and in one embodiment in the range from about 150° C. to about 200° C., and in one embodiment in the range from about 150° C. to about 190° C.

The term "end-of-run" (EOR) refers to the point in time when a production run is considered to be no longer economical. In one embodiment, the term end-of-run refers to the point in time during a production run when the average temperature in the reaction zone of a reactor exceeds about 265° C. In one embodiment, the term end-of-run refers to the point in time during a production run when in order to maintain a selectivity to ethylene oxide of at least about 80%, and in one embodiment at least about 82%, and in one embodiment at least about 84%; and/or the rate of production of ethylene oxide decreases to a level below about 245 kilograms of ethylene oxide per cubic meter of catalyst, and in one embodiment below about 240 kilograms of ethylene oxide per cubic meter of catalyst, and in one embodiment below about 235 kilograms of ethylene oxide per cubic meter of catalyst, and in one embodiment below about 230 kilograms of ethylene oxide per cubic meter of catalyst, and in one embodiment below about 225 kilograms of ethylene oxide per cubic meter of catalyst, or below about 220 kilograms of ethylene oxide per cubic meter of catalyst.

The term "ton" is used herein to refer to a metric ton (i.e., 1000 kilograms or 2204.6 pounds). The term "kiloton" or "kt" refers to 1000 metric tons.

Preferable the inventive process is conducted wherein the production run continues until at least about 0.5 kilotons of ethylene oxide are produced per cubic meter of catalyst.

Preferable the inventive process is conducted wherein ethylene oxide is produced at a rate of at least about 350 kilograms of ethylene oxide per cubic meter of catalyst per hour.

Preferable the inventive process is conducted wherein ethylene oxide is produced at a rate of at least about 250 kilograms of ethylene oxide per cubic meter of catalyst per hour and the selectivity to ethylene oxide being at least about 82%, maintaining an average temperature in the reaction zone below about 220° C.

Preferable the inventive process is conducted wherein ethylene oxide is produced at a rate of at least about 250 kilograms of ethylene oxide per cubic meter of catalyst per hour and the selectivity to ethylene oxide being at least about 82%, maintaining an average temperature in the reaction zone above about 265° C.

Preferable the inventive process is conducted wherein the average temperature in the reaction zone at the start of the production run is at least about 150° C.; increasing the temperature in the reaction zone during the production run at a sufficient rate to maintain an average production rate of at least about 250 kilograms of ethylene oxide per cubic meter of catalyst per hour.

The catalyst life provided by the inventive process may be at least about 2 times longer than with the same catalyst in a conventional process. In one embodiment, the catalyst life may be at least about 2.2, and in one embodiment at least about 2.5, and in one embodiment at least about 2.7, times longer than with the same catalyst in a conventional process. Thus, with the inventive process, in one embodiment, the reactor may be operated at least about 2 times longer between catalyst change outs, and/or at least about 2 times, and in one embodiment at least about 3 times, and in one embodiment at least about 4 times, more ethylene oxide may be produced by the same volume of catalyst before it needs to be changed due to loss of activity, selectivity, or both activity and selectivity.

The selectivity to ethylene oxide may be in the range from about 75 to about 95%, and in one embodiment from about 80 to about 95%, and in one embodiment in the range from about 85 to about 95%, and in one embodiment in the range from about 88 to about 92%.

The production rate or catalyst work rate for the inventive process may be at least about 250 kilograms of ethylene oxide per cubic meter of catalyst per hour ($kg/m^3_{cat}/hr$), and in one embodiment at least about 300 kilograms of ethylene oxide per cubic meter of catalyst per hour, and in one embodiment at least about 350 kilograms of ethylene oxide per cubic meter of catalyst per hour, and in one embodiment at least about 400 kilograms of ethylene oxide per cubic meter of catalyst per hour. The production rate of ethylene oxide may be in the range from about 250 to about 5000 kilograms per cubic meter of catalyst per hour, and in one embodiment in the range from about 300 to about 5000 kilograms per cubic meter of catalyst per hour, and in one embodiment in the range from about 350 to about 5000 kilograms per cubic meter of catalyst per hour, and in one embodiment in the range from about 400 to about 5000 kilograms per cubic meter of catalyst per hour, and in one embodiment in the range from about 500 to about 5000 kilograms per cubic meter of catalyst per hour.

The catalyst productivity for the inventive process may be at least about 0.5 kiloton of ethylene oxide produced per cubic meter of catalyst ($kt_{EO}/m^3_{cat}$), and in one embodiment at least about 1 kiloton of ethylene oxide per cubic meter of catalyst, and in one embodiment at least about 2 kilotons of ethylene oxide per cubic meter of catalyst, and in one embodiment at least about 3 kilotons of ethylene oxide per cubic meter of catalyst, and in one embodiment at least about 4 kilotons of ethylene oxide per cubic meter of catalyst. The catalyst productivity may be from about 0.5 to 10 kilotons of ethylene oxide per cubic meter of catalyst, and in one embodiment from about 1 to about 10 kilotons of ethylene oxide per cubic meter of catalyst, and in one embodiment from about 1 to about 8 kilotons of ethylene oxide per cubic meter of catalyst, and in one embodiment from about 1 to about 6 kilotons of ethylene oxide per cubic meter of catalyst, and in one embodiment from about 1 to about 4 kilotons of ethylene oxide per cubic meter of catalyst, and in one embodiment from about 2 to about 4 kilotons of ethylene oxide per cubic meter of catalyst.

The production rate or catalyst work rate for the inventive process may be at least about 250 $kg/m^3_{cat}/hr$ and the selectivity to ethylene oxide may be at least about 88%, and in one embodiment from about 88 to about 92%. The catalyst productivity may be at least about 1 $kt_{EO}/m^3_{cat}$.

The production rate or catalyst work rate may be at least about 250 $kg/m^3_{cat}/hr$, the selectivity to ethylene oxide may be at least about 87%, and the catalyst productivity may be at least about 2 $kt_{EO}/m^3_{cat}$.

The production rate or catalyst work rate may be at least about 250 $kg/m^3_{cat}/hr$, the selectivity to ethylene oxide may be at least about 85%, and the catalyst productivity may be at least about 3 $kt_{EO}/m^3_{cat}$.

The production rate or catalyst work rate may be at least about 250 $kg/m^3_{cat}/hr$, the selectivity to ethylene oxide may be at least about 83%, and the catalyst productivity may be at least about 4 $kt_{EO}/m^3_{cat}$.

The present invention relates to a process, comprising: reacting ethylene and oxygen or a source of oxygen in the presence of a catalyst in a reactor to form a product comprising ethylene oxide at a rate of at least about 250 $kg/m^3_{cat}/hr$, the selectivity to ethylene oxide being at least about 84%, the catalyst being in a reaction zone of the reactor and maintaining an average temperature in the reaction zone below about 220° C., wherein the catalyst contains silver or silver oxide and a support and the catalyst is in the form of particulate solids having a mean particle diameter from 1 to 1000 µm and wherein the molar ratio of oxygen to ethylene is from 1:4 to 10:1.

The present invention relates to a process, comprising: reacting ethylene and oxygen or a source of oxygen in the presence of a catalyst in a reactor to form a product comprising ethylene oxide at a rate of at least about 350 $kg/m^3_{cat}/hr$, the selectivity to ethylene oxide being at least about 80%, the catalyst being in a reaction zone of the reactor; and maintaining an average temperature in the reaction zone below about 220° C., wherein the catalyst contains silver or silver oxide and a support and the catalyst is in the form of particulate solids having a mean particle diameter from 1 to 1000 µm and wherein the molar ratio of oxygen to ethylene is from 1:4 to 10:1.

The present invention relates to a process, comprising reacting ethylene and oxygen or a source of oxygen in the presence of a catalyst in a reactor to form a product comprising ethylene oxide at a rate of at least about 350 $kg/m^3_{cat}/hr$, the selectivity to ethylene oxide being at least about 84%, the catalyst being in a reaction zone of the reactor; and maintaining an average temperature in the reaction zone below about 220° C., wherein the catalyst contains silver or silver oxide and a support and the catalyst is in the form of particulate solids having a mean particle diameter from 1 to 1000 µm and wherein the molar ratio of oxygen to ethylene is from 1:4 to 10:1.

The present invention relates to a process, comprising reacting ethylene and oxygen or a source of oxygen in the presence of a catalyst in a reactor to form a product comprising ethylene oxide at a rate of at least about 250 $kg/m^3_{cat}/hr$, the selectivity to ethylene oxide being at least about 84%, the catalyst being in a reaction zone of the reactor; and maintaining an average temperature in the reaction zone above about 265° C., wherein the catalyst contains silver or silver oxide and a support and the catalyst is in the form of particulate solids having a mean particle diameter from 1 to 1000 µm and wherein the molar ratio of oxygen to ethylene is from 1:4 to 10:1.

The present invention relates to a process, comprising reacting ethylene and oxygen or a source of oxygen in the presence of a catalyst in a reactor to form a product comprising ethylene oxide at a rate of at least about 350 $kg/m^3_{cat}/hr$, the selectivity to ethylene oxide being at least about 80%, the catalyst being in a reaction zone of the reactor; and maintaining an average temperature in the reaction zone above about 265° C., wherein the catalyst contains silver or silver oxide and a support and the catalyst is in the form of particulate solids having a mean particle diameter from 1 to 1000 μm and wherein the molar ratio of oxygen to ethylene is from 1:4 to 10:1.

The present invention relates to a process, comprising reacting ethylene and oxygen or a source of oxygen in the presence of a catalyst in a reactor to form a product comprising ethylene oxide at a rate of at least about 350 kg/m$^3_{cat}$/hr, the selectivity to ethylene oxide being at least about 84%, the catalyst being in a reaction zone of the reactor; and maintaining an average temperature in the reaction zone above about 265° C., wherein the catalyst contains silver or silver oxide and a support and the catalyst is in the form of particulate solids having a mean particle diameter from 1 to 1000 μm and wherein the molar ratio of oxygen to ethylene is from 1:4 to 10:1.

The catalyst used contains silver or silver compound and a support.

The porous support may have a porosity of at least about 5% as measured by mercury porosimetry and an average pore size (sum of pore diameters divided by number of pores) of about 1 to about 1000 μm. The porous support may be a porous ceramic or a metal foam. Other porous supports that may be used include carbides, nitrides, and composite materials. The porous support may have a porosity of about 30% to about 99%, and in one embodiment about 50% to about 98%. The porous support may be in the form of foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The support may comprise materials such as alpha-alumina, charcoal, pumice, magnesia, zirconia, titania, kieselguhr, fuller's earth, silicon carbide, silica, silicon carbide, clays, artificial zeolites, natural zeolites, ceramics and combination thereof. The preferred support is comprised of alpha-alumina having a very high purity; i.e., at least 95 wt. % pure, or more preferably, at least 98 wt. % alpha-alumina. The remaining components may include aluminas other than alpha-alumina or silica, alkali metal oxides (e.g., sodium oxide) and trace amounts of other metal-containing or non-metal-containing additives or impurities. A wide variety of such supports are commercially available. Suitable alumina carriers are manufactured and generally commercially available from Süd-Chemie Inc., Saint-Gobain Norpro or CeramTec AG.

The support may have a surface area, as measured by BET, of from about 0.01 to about 10 m$^2$/g, preferable of from about 0.05 to about 5 m$^2$/g, more preferable of from about 0.1 to about 3 m$^2$/g The catalytically active portion of the catalyst (active composition) may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces there between. The term "Wad" is used herein to refer to a structure of tangled strands, like steel wool. The active composition of the catalyst may be supported on a honeycomb structure.

The active composition of the catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow.

The active composition of the catalyst may be supported on a flow-through support structure such as a foam, wad, pellet, powder, or gauze.

The support structure for a flow-through catalyst may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 50% by weight of silver, expressed as metal, based on the total weight of the catalyst including the support. The silver is deposited upon the surface and throughout the pores of a porous refractory support. Silver contents, expressed as metal, of from about 1% to about 45% based on the total weight of the catalyst are preferred, while silver contents of from about 10% to about 40% are more preferred, while silver contents of from about 10% to about 35% are most preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support, either prior to, coincidentally with, or subsequent to the deposition of the silver may be a promoting amount of a metal, metal oxide or mixed metal oxide. The metal may be Mo, Re, W, V, Nb, Sb, Sn, Pt, Pd, Cs, Zr, Cr, Mg, Mn, Ni, Co, Ce, Ti, Hf, Tl, Th, Ga, Ge, Cu, Zn, Rh, Ru, Fe or a mixture of two or more thereof, preferable Mo, Re, W, Cr, Ti, Hf, Zr, V, TI, Th, Ta, Nb, Ga, Ge, or a mixture of two or more thereof. The catalyst may comprise sulfur, or an oxide thereof. These catalysts may also comprise one or more alkali metals or alkaline earth metals or other transition metals, rare earth metals, or lanthanides. The alkali metal may comprise lithium, cesium, potassium, rubidium and a mixture thereof, preferable lithium or cesium, most preferable cesium. The alkaline earth metal may comprise magnesium, barium, calcium or mixtures thereof. Additionally elements such as P and Bi may be present.

In one embodiment no promoting amount of rhenium is used, preferable the catalyst is free of rhenium. In this case the contamination of rhenium may be less than 0.01 mmol rhenium/kg catalyst.

The catalyst may comprises at least one further metal comprises one or more alkali metals, alkaline earth metals, molybdenum, tungsten, chromium, titanium, hafnium, zirconium, vanadium, thallium, thorium, tantalum, niobium, gallium, germanium or a mixture of two or more thereof.

The catalyst active composition may be any of the catalysts compositions disclosed in the following patents for use in converting ethylene to ethylene oxide: U.S. Pat. Nos. 4,908,343; 5,597,773; 5,703,253; 5,705,661; 6,762,311 B2; and EP 0266015 B1; these patents are incorporated herein by reference.

All promoters may be present in an amount of each of from about 0.001 wt. % to about 1 wt. %, preferably from about 0.005 wt. % to about 0.5 wt. %, and more preferably from about 0.01 wt. % to about 0.1 wt. % based on the weight of the total catalyst including the support.

The olefin epoxidation catalyst may comprise from about 1 to about 50 weight-% silver based on the total weight of the catalyst and from about 20 to about 1000 ppm lithium. Preferable the olefin epoxidation catalyst may comprise from about 10 to about 35% silver and from about 50 ppm to about 400 ppm lithium.

The olefin epoxidation catalyst may comprise from about 1 to about 50 weight-% silver based on the total weight of the catalyst and from about 20 to about 1000 ppm cesium.

Preferable the olefin epoxidation catalyst may comprise from about 10 to about 35% silver and from about 100 ppm to about 600 ppm cesium.

The olefin epoxidation catalyst may comprise from about 1 to about 50 weight-% silver based on the total weight of the catalyst and from about 0 to about 1000 ppm rhenium. Preferable the olefin epoxidation catalyst may comprise from about 10 to about 35% silver and from about 0 ppm to about 500 ppm rhenium.

The olefin epoxidation catalyst may comprise further from about 0 to 200 ppm sulfur, preferable from about 0 to about 100 ppm sulfur.

The olefin epoxidation catalyst may comprise from about 10 to about 15 weight-% silver based on the total weight of the catalyst, from about 350 to about 450 ppm cesium, from about 50 to about 130 ppm tungsten, from about 150 to about 400 ppm rhenium, from about 150 to about 200 ppm lithium and from about 0.005 to about 0.015 weight-% based on the total weight of the catalyst potassium.

The catalyst's active composition comprises preferable essentially silver and a promoting amount of cesium. The olefin epoxidation catalyst may comprise from about 25 to about 40 weight-% silver based on the total weight of the catalyst, from about 300 to about 500 ppm cesium.

The catalyst composition may comprise a silver based catalyst such as the silver based catalyst disclosed in EP 0 496 470 B1, which is incorporated herein by reference. This catalyst comprises silver and may comprise one or more alkali metal promoters, one or more rhenium promoters, and optionally one or more rhenium co-promoters selected from sulfur, molybdenum, tungsten, chromium, or a mixture of two or more thereof. The active composition of the catalyst is supported on a support. The support may comprise at least about 85% by weight, and in one embodiment at least about 90% by weight of alpha alumina, from about 0.01 to about 6% by weight (measured as the oxide) of an alkaline earth metal in the form of an oxide, from about 0.01 to about 5% by weight (measured as the dioxide) of silicon in the form of an oxide, and from zero to about 10% by weight, and in one embodiment from about 0.1 to about 10% by weight (measured as the dioxide) of zirconium in the form of an oxide. The alkaline earth metal may comprise calcium and/or magnesium.

The catalyst composition may comprise a silver based catalyst such as the silver based catalyst disclosed in EP 1 292 587 B1, which is incorporated herein by reference. This catalyst contains a catalytically effective amount of silver and may contain a promoting amount of rhenium or compound thereof, a promoting amount of at least one further metal or compound thereof and optionally a co-promoting amount of a rhenium co-promoter which can be selected from one or more of sulfur, phosphorus, boron, and compounds thereof, on a refractory support. The at least one further metal may comprise one or more alkali metals, alkaline earth metals, molybdenum, tungsten, chromium, titanium, hafnium, zirconium, vanadium, thallium, thorium, tantalum, niobium, gallium and germanium and mixtures thereof. The at least one further metal may comprise lithium, potassium, rubidium, cesium, calcium and/or barium. The at least one further metal may comprise lithium, potassium and/or cesium. The components of these catalysts may have a concentration, when calculated as the element in grams (g), milligrams (mg) or millimoles (mmol) per kilogram (kg) of the total catalyst, of silver at a concentration in the range from about 10 to about 300 g/kg, rhenium at a concentration in the range from about 0.01 to about 15 mmol/kg, one or more further metals at a concentration in the range from about 10 to about 3000 mg/kg, and one or more optional rhenium co-promoters at a concentration in the range from about 0.1 to about 10 mmol/kg.

The catalyst is in the form of particulate solids (e.g., pellets, powder, fibers, and the like) having a median particle diameter ($D_{70}$) of about 1 to about 1000 μm (microns), and in one embodiment from about 25 to about 500 μm, and in one embodiment from about 50 to about 350 μm, and in one embodiment from about 75 to about 300 μm. In one embodiment, the catalyst is in the form of a fixed bed of particulate solids.

The catalyst may be in the form of a bed of particulate solids positioned in a reaction zone wherein one or more interior walls of the reaction zone may include additional catalyst washcoated and/or grown thereon. The catalyst in the bed of particulate solids may be the same as the catalyst washcoated and/or grown on the interior walls of the reaction zone, or it may be different.

The catalyst may be in the form of one or more pieces of porous contiguous material. In one embodiment, the catalyst may be comprised of a contiguous material and has a contiguous porosity such that molecules can diffuse through the catalyst. In this embodiment, the fluids flow through the catalyst rather than around it. In one embodiment, the cross-sectional area of the catalyst occupies about 1 to about 99%, and in one embodiment about 10 to about 95% of the cross-sectional area of the reactor.

The catalyst may have a surface area, as measured by BET, of greater than about 0.5 $m^2/g$, and in one embodiment greater than about 2 $m^2/g$.

The catalyst may be regenerated. This may be done by flowing a regenerating fluid through the reactor in contact with the catalyst. The regenerating fluid may comprise hydrogen or a diluted hydrogen stream, oxygen or an oxygen containing stream, or a stream containing a halogen containing gas or a mixture of oxygen and a halogen containing gas. Halogen compounds may include metal halides and organic halides. The diluent may comprise nitrogen, argon, helium, methane, ethylene, carbon dioxide, steam, or a mixture of two or more thereof. The regenerating fluid may flow from the header through the reactor and to the footer, or in the opposite direction from the footer through the reactor to the header. The temperature of the regenerating fluid may be from about 50 to about 400° C., and in one embodiment about 200 to about 350° C. The pressure within the reactor during this regeneration step may range from about 1 to about 40 bars, and in one embodiment about 1 to about 20 bars, and in one embodiment about 1 to about 5 bars. The residence time for the regenerating fluid in the reactor may range from about 0.01 to about 1000 seconds, and in one embodiment about 0.1 second to about 100 seconds.

The catalyst may be segregated into separate reaction zones in the reactor in the direction of flow through the reactor. The same or different catalyst or catalyst composition may be used in each reaction zone. In each reaction zone the length of one or more adjacent heat exchange zone(s) may vary in their dimensions. For example, in one embodiment, the length of the one or more adjacent heat exchange zones may be less than about 50% of the length of each reaction zone. Alternatively, the one or more heat exchange zones may have lengths that are more than about 50% of the length of each reaction zone up to about 100% of the length of each reaction zone.

The catalyst may be in the form of a catalyst bed that may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The bed fraction may range from 100% by weight active catalyst to less than 50% by weight active catalyst. In an alternate embodiment the thermally conductive inert material may be deployed at the center or within the catalyst particles. The active catalyst may be deposited on the outside, inside or intermittent within a composite structure that includes the thermally conductive inert. The resulting catalyst composite structure may have an effective thermal conductivity when placed in a reactor that is at least about 0.5 W/m/K, and in one embodiment at least about 1 W/m/K, and in one embodiment at least about 2 W/m/K.

In one embodiment, the catalyst may be in the form of a catalyst bed that may be graded only locally within the reactor. For example, a reactor may contain a catalyst bed with a first reaction zone and a second reaction zone. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products. The catalyst may be graded with an inert material in the first and/or second reaction zone, in full or in part. The first reaction zone may contain a first composition of catalyst or inert material, while the second reaction zone may contain a second composition of catalyst or inert material.

In one embodiment, different particle sizes may be used in different axial length regions of the reactor to provide for graded catalyst beds. For example, very small particles may be used in a first reaction zone while larger particles may be used in a second reaction zone. The very small particles may be in the range from about 75 to about 350 μm. Larger particles may cause lower pressure drops per unit length of the reactor and may also reduce the catalyst effectiveness. The effective thermal conductivity of the catalyst bed may be lower for larger size particles. Smaller particles may be used in regions where improved heat transfer is sought throughout the catalyst bed or alternatively larger particles may be used to reduce the local rate of heat generation.

The reactants or process feed may comprise ethylene and oxygen or a source of oxygen. A mixture of the ethylene and oxygen or a source of oxygen may be referred to as a reactant composition. The ethylene may be combined with the oxygen or source of oxygen in the reactor or upstream of the reactor. The purity of the reactants may not be critical, although it is desirable to avoid the presence of compounds which may poison the catalyst.

The reactants or process feed may further comprise one or more organic halides. The organic halide may comprise one or more alkyl and/or alkylene halides, for example, ethyl chloride and/or vinyl chloride, and the like. The organic halides may be used as promoters for the conversion of ethylene and oxygen to ethylene oxide. The alkyl groups may contain from 1 to about 5 carbon atoms, and in one embodiment from 1 to about 3 carbon atoms. The alkylene groups may contain from 2 to about 5 carbon atoms, and in one embodiment from 2 to about 3 carbon atoms. The halides may comprise chloride, bromide and/or iodide. The halide may comprise chloride.

The oxygen or source of oxygen may comprise molecular oxygen, air and/or other oxidants, such as nitrogen oxides (e.g., NO, $N_2O$), which may function as sources of oxygen. The source of oxygen may comprise oxygen enriched air. The source of oxygen may comprise a mixture of oxygen and/or air, and carbon dioxide. Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used.

The reactants or process feed may comprise from about 5 to about 75% by volume ethylene on a whole feed basis, and in one embodiment from about 5 to about 65%, and in one embodiment from about 5 to about 55%, and in one embodiment from about 5 to about 50% by volume ethylene. The reactants or process feed may comprise at least about 5% by volume oxygen or a source of oxygen on a whole feed basis, and in one embodiment from about 5 to about 95% by volume, and in one embodiment from about 5 to about 50% by volume, and in one embodiment from about 10 to about 25% by volume oxygen or a source of oxygen. The mole ratio of oxygen or source of oxygen to ethylene on a whole feed basis may be in the range from about 1:4 to about 10:1, and in one embodiment from about 1:3 to about 7:1, and in one embodiment from about 1:3 to about 5:1, and in one embodiment from about 1:3 to about 2:1, and in one embodiment from about 1:2 to about 1:1. The reactants or process feed may contain up to about 100 parts per million (ppm) by volume on a whole feed basis of one or more organic halides, and in one embodiment in the range from about 0.3 to about 100 ppm, and in one embodiment in the range from about 0.3 to about 70 ppm, and in one embodiment from about 0.3 to about 50 ppm, and in one embodiment from about 0.3 to about 25 ppm, and in one embodiment from about 1 to about 10 ppm.

The reactants or process feed may include one or more diluent materials. The diluent materials may include nitrogen, helium, methane, natural gas, carbon dioxide, liquid water, steam, argon, and the like. The diluent materials may be mixed with the ethylene, the oxygen or source of oxygen, or a mixture of both the ethylene and the oxygen or source of oxygen. The volume ratio of diluent to ethylene and/or oxygen or source of oxygen may be in the range from zero to about 80% by volume. The concentration of carbon dioxide may be in the range up to about 5% by volume, and in one embodiment up to about 3% by volume, and in one embodiment up to about 1% by volume. However, an advantage of at least one embodiment of the invention is that it is possible to conduct the inventive process without the use of such diluents or with a reduced amount of such diluents, thus a more efficient and compact process may be provided.

The reactants or process feed may comprise on a whole feed basis from about 5% to about 95% by volume of oxygen, from about 3% to about 75% by volume of ethylene, from about 0% to about 80% by volume of one or more diluent materials, and up to about 100 ppm by volume of one or more organic halides.

The reactants or process feed may further comprise a recycle stream from which ethylene oxide, and optionally other components, have been separated out.

The contact time of the process fluids with the catalyst within the reactor may range from about 50 to about 900 milliseconds (ms), and in one embodiment from about 100 to about 900 ms, and in one embodiment from about 100 to about 500 ms, and in one embodiment from about 100 to about 300 ms, and in one embodiment from about 150 to about 300 ms.

The space velocity (or gas hourly space velocity) for the flow of process fluid through the reactor may be in the range from about 1000 to about 50,000 liter of feed per liter of catalyst per hour ($hr^{-1}$). The space velocity may range from about 2500 to about 35,000 $hr^{-1}$, and in one embodiment from about 5000 to about 25,000 $hr^{-1}$.

In one embodiment, the conversion of ethylene to ethylene oxide may be accompanied by the formation of carbon dioxide (for example, selectivities of about 80% ethylene oxide and 20% $CO_2$). The activation energy to form ethylene oxide may be lower than that to form carbon dioxide.

The local conditions in the reactor may be controlled via tailoring temperature and/or composition profiles via one or more of the following: heat exchange with heat exchange channels adjacent to the one or more channels in the reactor; heat exchange with heat exchange channels in thermal contact with the channels; heat exchange with multiple combinations of heat exchange channels strategically placed to correspond to individual reactor sections; addition of one or more reactants and/or diluents using staged addition along the axial length of the channels.

An isothermal reactor profile may be employed. With such a thermal profile, a partial boiling heat exchange fluid may be used.

A tailored temperature profile along the length of the reactor may be used.

In order to control the exothermic reaction via heat exchange with a heat exchange medium, for example, heat exchange fluid, the process may employ a heat flux at or near the entrance to the reactor that is higher than the heat flux near the outlet of the reactor.

The reactants may be preheated prior to entering the reactor. The reactants may be preheated to the average temperature employed in reaction zone of the one or more channels used reactor. The reaction process is exothermic. In order to control the reaction, heat is transferred from the process channels to a heat exchange medium. That is, during the inventive process the process channels are cooled using a heat exchange medium. The heat exchange medium may comprise a heat exchange fluid in one or more heat exchange channels. The heat channels may be adjacent to and/or in thermal contact with the process channels. The heat exchange fluid absorbs heat from the process channels, and then flows out of the heat exchange channels into and through the heat exchange manifold. Heat transfer between the process fluids and heat exchange fluid may be effected using convective heat transfer.

In one embodiment, heat transfer may be enhanced using a heat exchange fluid wherein the heat exchange fluid undergoes an endothermic reaction and/or a full or partial phase change (e.g., partial boiling). Multiple heat exchange zones may be employed along the length of the process channels to provide for different temperatures at different locations along the axial lengths of the process channels. Also, at the end of the reaction the product may be quenched in order to reduce or eliminate the formation of undesired by-products. Quenching may be effected in the channel reactor or downstream of the reactor known by the person skilled in the art.

The cooling of the reactor during the inventive process, in one embodiment, is advantageous for controlling selectivity towards the main or desired product due to the fact that such added cooling reduces or eliminates the formation of undesired by-products from undesired parallel reactions with higher activation energies. As a result of this cooling, in one embodiment, the temperature of the reactants at the entrance to the reactor may be within about 20° C., and in one embodiment within about 10° C., and in one embodiment within about 5° C., and in one embodiment within about 3° C., and in one embodiment within about 2° C., and in one embodiment within about 1° C., of the temperature of the product (or mixture of product and unreacted reactants) at the outlet of the reactor. In one embodiment, the reactor may be operated with an isothermal or substantially isothermal temperature profile.

The average temperature of the process fluids in the rector may be in the range from about 150° C. to about 265° C., and in one embodiment from about 180° C. to about 265° C., and in one embodiment from about 200° C. to about 265° C., and in one embodiment from about 220° C. to about 265° C.

The pressure in the reactor may be in the range from about 5 to about 30 bars, and in one embodiment from about 10 to about 20 bars.

The pressure drop for the process fluids as they flow in the reactor may range up to about 2 bars per foot of length of the reactor (bars/ft), and in one embodiment up to about 1.5 bars/ft, and in one embodiment up to 1 bars/ft, and in one embodiment up to about 0.5 bars/ft.

The flow of the process fluids in the reactor may be laminar or in transition, and in one embodiment it is laminar. The Reynolds Number for the flow of process fluids in the reactor may be up to about 4000, and in one embodiment up to about 2300, and in one embodiment in the range of about 10 to about 2000, and in one embodiment about 100 to about 1500.

The superficial velocity for the process fluids flowing in the process channels may be at least about 0.01 meters per second (m/s), and in one embodiment in the range from about 0.01 to about 5 m/s, and in one embodiment in the range from about 0.01 to about 2 m/s, and in one embodiment in the range from about 0.01 to about 1 m/s, and in one embodiment in the range from about 0.05 to about 0.5 m/s.

The free stream velocity for process fluid flowing in the process channels may be at least about 0.001 m/s, and in one embodiment at least about 0.01 m/s, and in one embodiment in the range from about 0.001 to about 200 m/s, and in one embodiment in the range from about 0.01 to about 100 m/s, and in one embodiment in the range from about 0.01 to about 200 m/s.

The level of conversion of the ethylene per pass through the reactor may be up to about 10%, and in one embodiment up to about 20%, and in one embodiment up to about 30%, and in one embodiment up to about 40%, and in one embodiment up to about 50%.

The level of conversion of oxygen per pass through the reactor may be up to about 10%, and in one embodiment up to about 20%, and in one embodiment up to about 30%, and in one embodiment up to about 40%, and in one embodiment up to about 50% or higher.

The yield of ethylene oxide may be up to about 10% per cycle, and in one embodiment up to about 20%, and in one embodiment up to about 30%, and in one embodiment up to about 40%, and in one embodiment about 50% per cycle. The term "cycle" is used herein to refer to a single pass of the reactants through the reactor.

In one embodiment, the level of conversion of the ethylene may be up to about 10%, and the level of selectivity to ethylene oxide may be in the range from about 75% to about 95%.

In one embodiment, the level of conversion of the ethylene may be up to about 20%, and the level of selectivity to ethylene oxide may be in the range from about 75% to about 95%.

In one embodiment, the level of conversion of the ethylene may be up to about 30%, and the level of selectivity to ethylene oxide may be in the range from about 75% to about 95%.

In one embodiment, the level of conversion of the ethylene may be up to about 40%, and the level of selectivity to ethylene oxide may be in the range from about 75% to about 95%.

A production run may be started after the catalyst, reactor and one or more of the reactants are allowed to undergo a conditioning period of up to about 500 hours, and in one embodiment up to about 400 hours, and in one embodiment up to about 300 hours, and in one embodiment up to about 200 hours. During this conditioning period the catalyst, reactor and one or more reactants may be permitted to achieve an equilibrium temperature. The process may be commenced during the conditioning period to allow the production rate to build to a desired level prior to the start of a production run (SOR). The start of a production run may be commenced when an average production rate of at least about 250 kilograms of ethylene oxide per cubic meter of catalyst per hour ($Kg/m^3_{cat}/hr$) is established. The start-of-run temperature ($T_{SOR}$) for a production run may be in the range from about 150° C. to about 265° C., and in one embodiment in the range from about 150° C. to about 250° C., and in one embodiment in the range from about 150° C. to about 240° C., and in one embodiment in the range from about 150° C. to about 230° C., and in one embodiment in the range from about 150° C. to about 220° C., and in one embodiment in the range from about 150° C. to about 210° C., and in one embodiment in the range from about 150° C. to about 200° C., and in one embodiment in the range from about 150° C. to about 190° C. After the start of the production run, the temperature in the reaction zone may be relatively constant, but allowed to increase gradually to compensate for gradual deactivation of the catalyst. In one embodiment, the average temperature in the reaction zone during a production run may not decrease by more than about 20° C., and in one embodiment not more than about 10° C., and in one embodiment not more than about 5° C., and in one embodiment not more than about 2° C.

The end of a production run (EOR) may occur when a maximum desired temperature ($T_{EOR}$) in the reaction zone is achieved. The end-of-run temperature may be about 265° C., and in one embodiment in the range from about 265° C. to about 270° C., and in one embodiment in the range from about 265° C. to about 280° C.

Alternatively, the end of a production run may occur when the selectivity to ethylene oxide and the rate of production of ethylene oxide decreases below a desired level. The end of a production run may occur when the selectivity to ethylene oxide decreases below about 84%, and in one embodiment below about 82%, and in one embodiment below about 80%; and/or the rate of production of ethylene oxide decreases to a level below about 245 kilograms of ethylene oxide per cubic meter of catalyst, and in one embodiment below about 240 kilograms of ethylene oxide per cubic meter of catalyst, and in one embodiment below about 235 kilograms of ethylene oxide per cubic meter of catalyst, and in one embodiment below about 230 kilograms of ethylene oxide per cubic meter of catalyst, and in one embodiment below about 225 kilograms of ethylene oxide per cubic meter of catalyst, and in one embodiment below about 220 kilograms of ethylene oxide per cubic meter of catalyst.

The inventive process may be conducted in any reactor wherein the contact times and heat and mass transfer characteristics that are suitable for achieving the production rates and selectivities to ethylene oxide discussed herein can be achieved. A preferred, and in fact highly advantageous, reactor for conducting the process would be a microchannel reactor (see WO 2008/030467, WO 2006/020709, WO 2007/071739 and US 2008/0031788, which are incorporated herein by reference). Other reactors that may be used for conducting the inventive process include fixed bed reactors (see US 2008/0081920), and fluidized bed reactors (see RD 470051), the foregoing references being incorporated herein by reference.

The heat exchange fluid may be any fluid. These include air, steam, liquid water, steam, gaseous nitrogen, other gases including inert gases, carbon monoxide, molten salt, oils such as mineral oil, a gaseous hydrocarbon, a liquid hydrocarbon, heat exchange fluids such as Dowtherm A and Therminol which are available from Dow-Union Carbide, or a mixture of two or more thereof.

The heat exchange fluid may comprise a stream of one or more of the reactants and/or the product. This can provide process cooling for the reactor and/or pre-heat for the reactants and thereby increase the overall thermal efficiency of the process.

The heat exchange fluid may undergo a partial or full phase change as it flows through the heat exchange channels. This phase change may provide additional heat removal from the process channels beyond that provided by convective cooling. For a liquid heat exchange fluid being vaporized, the additional heat being transferred from the process channels would result from the latent heat of vaporization required by the heat exchange fluid. An example of such a phase change would be a heat exchange fluid such as oil or water that undergoes partial boiling. In one embodiment, up to about 50% by weight of the heat exchange fluid may be vaporized.

The heat exchange fluid in the heat exchange channels may have a temperature in the range from about 100° C. to about 270° C., and in one embodiment from about 120° C. to about 250° C., and in one embodiment from about 140° C. to about 230° C. The difference in temperature between the heat exchange fluid and the process fluids in the process channel may be up to about 50° C., and in one embodiment up to about 30° C., and in one embodiment up to about 10° C. The residence time of the heat exchange fluid in the heat exchange channels may range from about 1 to about 1000 ms, and in one embodiment about 1 to about 500 ms, and in one embodiment from 1 to about 100 ms. The pressure drop for the heat exchange fluid as it flows in the heat exchange channels may be up to about 3 bar/ft, and in one embodiment up to about 1 bar/ft. The flow of the heat exchange fluid in the heat exchange channels may be laminar or in transition, and in one embodiment it is laminar. The Reynolds Number for the flow of heat exchange fluid in the heat exchange channels may be up to about 4000, and in one embodiment up to about 2300, and in one embodiment in the range of about 10 to about 2000, and in one embodiment about 10 to about 1500.

The control of heat exchange during the ethylene oxide-forming reaction process may be advantageous for controlling selectivity towards the desired product due to the fact that added cooling may reduce or eliminate the formation of undesired by-products from undesired parallel reactions with higher activation energies.

In one embodiment, the process may be conducted in a reactor containing a plurality of heat exchange channels operating in parallel. The total pressure drop for the heat exchange fluid flowing in the heat exchange channels may be up to about 10 bars, and in one embodiment up to about 5 bars, and in one embodiment up to about 2 bars.

The ethylene may be formed upstream of the reactor or it may be formed in the reactor. Part of the reactor may be used for ethylene formation and part of the reactor may be used for ethylene oxide formation. The ethylene may be formed in the reactor using catalytic oxidative dehydrogenation, catalytic dehydrogenation and/or thermal cracking.

The ethylene oxide may be converted into ethylene glycol. The ethylene glycol may be formed downstream of the reactor. The ethylene glycol may be formed in the reactor. Part of the reactor may be used for ethylene oxide formation and part of the reactor may be used for ethylene glycol formation.

The process may include the step of quenching the product. The product may be quenched downstream of the reactor. The product may be quenched in the reactor.

In one embodiment, a first portion of the reactor may be used for ethylene formation using thermal or catalytic cracking, followed by cooling in a second portion of the reactor, followed by conversion of the ethylene to form ethylene oxide in a third portion of the reactor. In one embodiment, oxidative dehydrogenation may be used in the reactor to form ethylene from ethane, followed by cooling, and then mixing the ethylene with oxygen and contacting a catalyst to form the ethylene oxide.

The reactors contain an ethylene forming catalyst and an olefin epoxidation catalyst, the ethylene forming catalyst being positioned upstream of the olefin epoxidation catalyst. Ethane and oxygen or a source of oxygen contact the ethylene forming catalyst and react to form ethylene. The product ethylene may be cooled. The ethylene and oxygen or source of oxygen may then contact the olefin epoxidation catalyst and react to form ethylene oxide. A heat exchange fluid is used to control temperature.

The ethylene oxide that is formed in the reactor may be converted to ethylene glycol.

The reactor may contain an olefin epoxidation catalyst and a glycol forming catalyst, the olefin epoxidation catalyst being positioned upstream of the glycol forming catalyst. Ethylene and oxygen or a source of oxygen contact the olefin epoxidation catalyst and react to form ethylene oxide. The ethylene oxide and water may then contact the glycol forming catalyst and react to form ethylene glycol.

The inventive process combines the advantages of a high selective process and a long lifetime of the catalyst. Consequently, the operating and catalyst costs can be reduced tremendously. In addition, the high selectivity can be obtained by a high active catalyst, thus, obtaining both the advantage of high activity and high selectivity.

The low SOR temperature allows a longer operation at the optimum maximal selectivity since the silver sintering is decelerated. This will offer an increase in the ethylene oxide productivity per volume of catalyst and per year. The difference in the average selectivity over a catalyst life is expected to exceed the 3% under the inventive process conditions compared to the conventional process conditions. The high ethylene oxide average selectivity may improve reactant composition or feedstock utilization at a reduced operating cost. In addition, the low SOR temperature allows a long lifetime of the catalyst.

As the inventive process in one embodiment is conducted with a reactant composition that is relatively close to stoichiometric; this provides the advantage of reduced separation costs, e.g., eliminating or reducing the requirement for a $CO_2$ scrubber. In addition, a greater throughput is achieved.

EXAMPLES

1. Reactor

A process for converting ethylene and oxygen to ethylene oxide is conducted using the microchannel reactor shown in FIG. 1. Referring to FIG. 1, microchannel reactor 500 includes microchannel reactor core 510, reactant inlet 520, product outlet 530, heat exchange fluid inlets 540 and 550, and heat exchange fluid outlets 560 and 570. The microchannel reactor core 510 is made of stainless steel. The microchannel reactor core 510 contains a single process microchannel and two heat exchange channels, the heat exchange channels being positioned on each side of the process microchannel.

Figure 2:
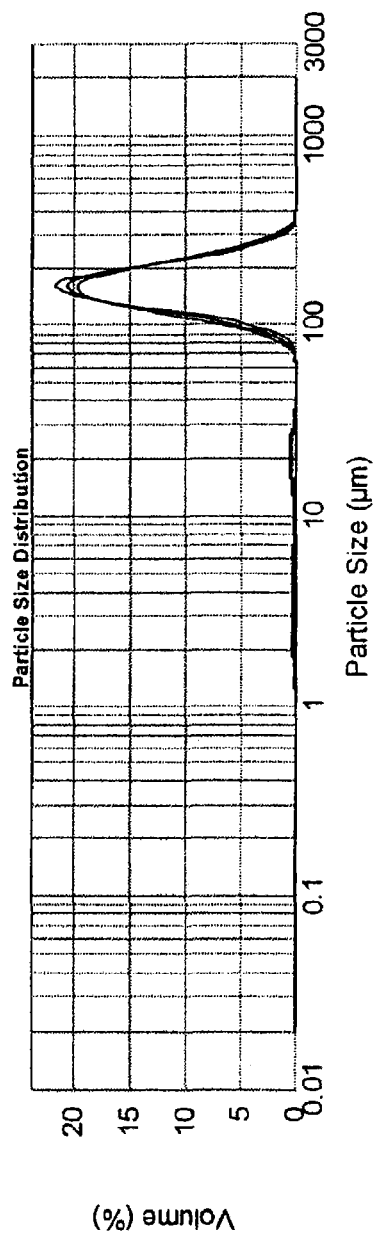
FIG. 2 shows the particle size distribution for three samples of the catalyst used in connection with the process.

The catalyst is crushed and sieved to obtain a particle size in the range of 125-150 µm. The particle size distribution for three samples of the catalyst is shown in FIG. 2. The catalyst is used in the form of a bed of particulate solids which is positioned in the microchannel reactor core 510. An inert particulate bed made of steatite particulates having an average diameter of 100 µm is packed in the process microchannel on each side of the catalyst bed. The length of each of the steatite beds is 0.64-0.74 cm. The bed of particulates (i.e., catalyst particulates and steatite particulates) is held in place with two stainless steel mesh screens positioned on each side of the bed. One of the screens has a 600 µm size and the other has a 75 µm size.

Figure 3:
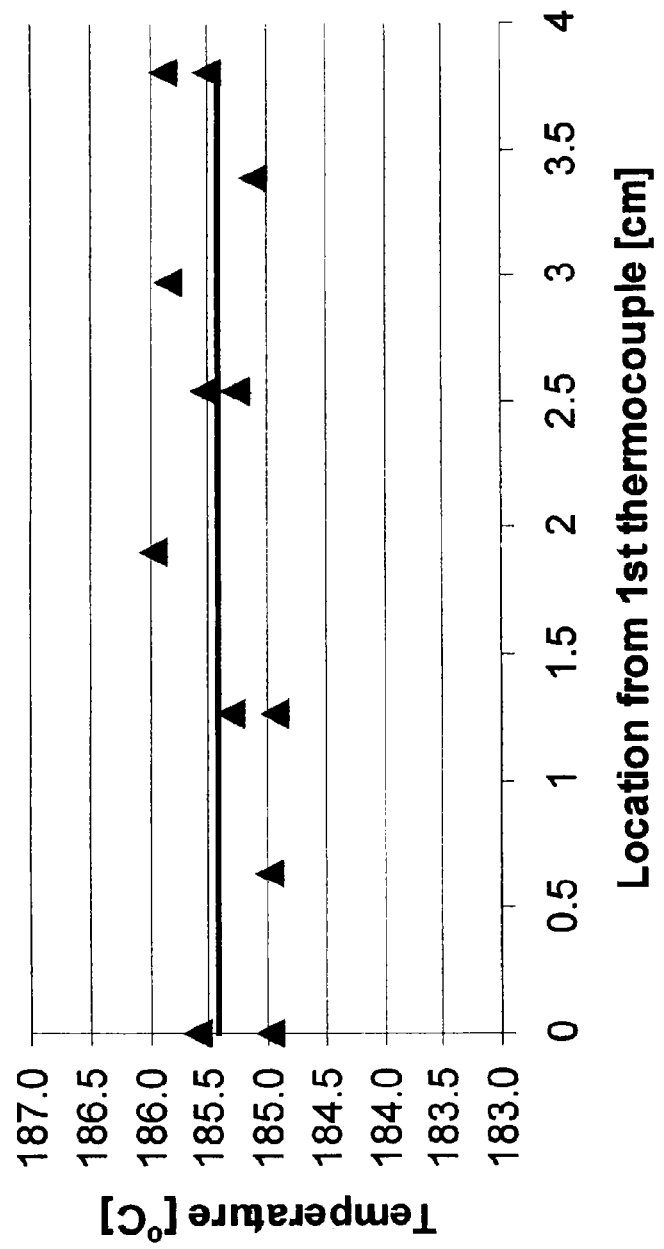
FIG. 3 shows the relationship between temperature (° C.) and distance (cm) from the first thermocouple for one test run.

The process microchannel has a rectangular cross section with an internal height of 0.635 mm or 0.95 mm as indicated below. The process microchannel has an internal width of 0.76 cm and a length of 6.99 cm. The heat exchange channels have rectangular cross sections with internal dimensions of 0.76 mm by 0.76 cm. The heat exchange fluid is Marlotherm SH (a heat transfer oil supplied by Sasol). The heat exchange fluid flows through the heat exchange channels at a rate of 5-7 liters per minute (lpm). The flow of the heat exchange fluid is turbulent and sufficient to provide the process microchannel with a substantially isothermal temperature profile. The microchannel reactor core 510 contains an array of 12 thermocouples for measuring temperature. The temperature measurements for one test run are shown in FIG. 3.

Ethylene, methane, carbon-dioxide and ethyl chloride doped methane are mixed using a set of flow controllers to form a reactant flow stream. There are two methane feed streams which are combined while forming the reactant flow stream. One of the methane feed streams is doped with ethyl chloride at a concentration of 20 ppm by volume. A separate flow stream of oxygen and nitrogen (tracer) is mixed with the reactant flow stream to form a combined feed stream. The combined feed stream enters the microchannel reactor as shown in FIG. 1, and undergoes a reaction to form a product containing ethylene oxide. The product flows out of the microchannel reactor 500 as shown in FIG. 1. The feed stream entering the microchannel reactor 500 and the product flowing out of the microchannel reactor 500 are analyzed using a Hewlett Packard 5890 series II gas chromatograph.

2. Catalyst Composition

The active composition of the catalyst was supported on an alpha-aluminum oxide support. The highly active catalyst (catalyst 1) contained 33 weight-% silver and 400 ppm Cs based on the total weight of the catalyst. The highly selective catalyst (catalyst 2) contained 13.7 weight-% Ag, 410 ppm Cs, 90 ppm W, 370 ppm Re and 180 ppm Li based on the total weight of the catalyst.

3. Examples

3.1 Example 1

Comparative test runs for converting ethylene to ethylene oxide were conducted under the same catalyst type (catalyst 2) and batch but under different operating conditions using a microchannel reactor. Comparison was made between catalyst performance using a ratio of ethylene to oxygen of 2:1 and catalyst activity using a ratio of ethylene to oxygen of 8:1.

For this production run, 0.37 g of a high selectivity type catalyst (catalyst 2) was used. The catalyst bed length was 5.4 cm. The catalyst volume was 0.395 ml. The reactant composition contained:

| Ratio (ethylene:oxygen) | 8:1 | 2:1 |
|---|---|---|
| Ethylene (Vol.-%) | 75 | 50 |
| Oxygen (Vol.-%) | 9 | 25 |
| GHSV ($hr^{-1}$) | 16 000 | 16 000 |
| EO Selectivity (%) | 88.4 | 89.6 |
| Pressure (absolute bar) | 16 | 16 |
| Work rate (ktEO/$m^3$cat/h) | 234 | 232 |
| Reactor Temperature (° C.) | 230 | 185 |
| Ethyl chloride (parts per million (ppm) by volume) | 2.2 | 2.2 |
| Nitrogen (mole %) | 5 | 5 |
| Methane | balance | balance |

The process comparison was conducted in the same reactor type but under two different operating conditions which are shown in the table above.

The main advantage of the inventive process is the low SOR temperature which (i) increase selectivity as side-reactions are decreased and (ii) increases life-time of the catalyst as the low SOR temperature contains a high potential for compensation of the deactivation of the catalyst.

3.2 Example 2

A comparison of the two different ethylene to oxygen ratios: the conventional process condition of 5:1 and the inventive process condition of 2:1 was carried out for a long time. The same high selectivity catalyst (catalyst 2) was used for this comparison. For the 5:1 process condition, 30 g of catalyst were loaded in a tubular reactor to provide a catalyst bed length of about 90 cm and for the 2:1 process condition 0.37 g. of a catalyst were loaded in the a microchannel reactor to provide a catalyst bed length of 5.4 cm.

The reactant composition contained:

| Ratio (ethylene:oxygen) | 5:1 | 2:1 |
|---|---|---|
| Ethylene (Vol.-%) | 35 | 50 |
| Oxygen (Vol.-%) | 7 | 25 |
| GHSV ($hr^{-1}$) | 5000 | 16000 |
| EO Selectivity (%) at 3000 h | ~89 | ~90.5 |
| Pressure (absolute bar) | 16 | 16 |
| Work rate (ktEO/$m^3$cat/h) | 250 | 250 |
| SOR Temperature (° C.) | 243 | 183 |
| Ethyl chloride (parts per million (ppm) by volume) | 2.5 | 2.2 |
| Nitrogen (mole %) | 0 | 5 |
| Methane | balance | balance |

Figure 4A:
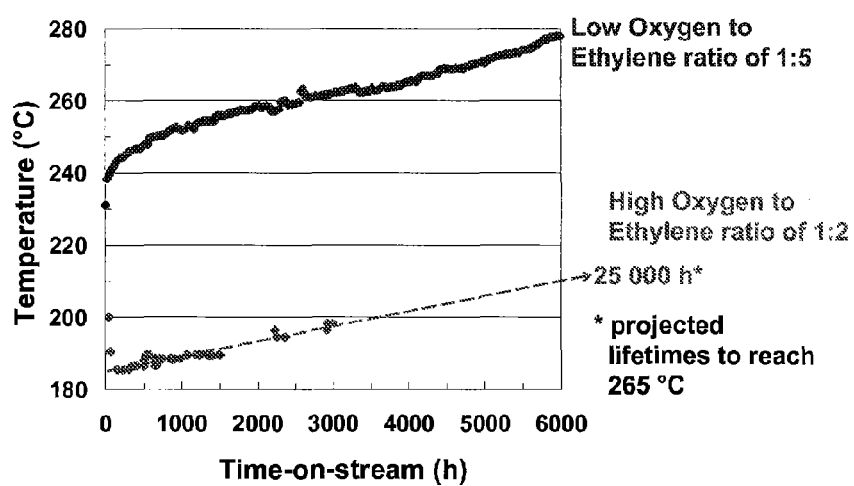
FIG. 4A shows the relationship between temperature (° C.) and time-on-stream (hours) for catalyst 2 under low and a high oxygen to ethylene ratios of 1:5 and 1:2, respectively.
Figure 4B:
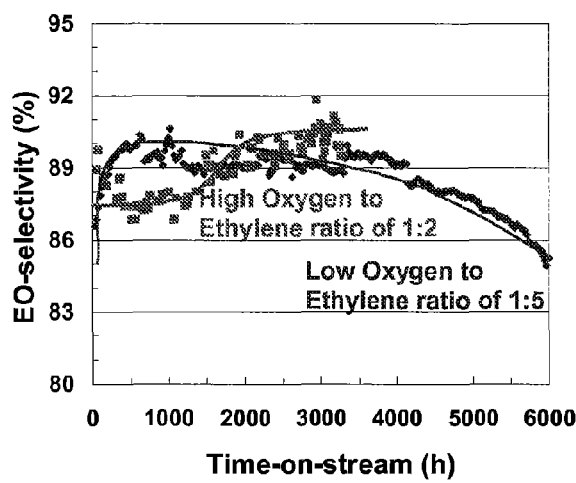
FIG. 4B shows the relationship between EO-selectivity (%) and time-on-stream (hours) for catalyst 2 under low and high oxygen to ethylene ratios of 1:5 and 1:2, respectively.

The results of the long term experiments are shown in FIG. 4A-B. Comparison was made between catalyst performance using a ratio of ethylene to oxygen of 2:1 and catalyst performance using a ratio of ethylene to oxygen of 5:1.

It is expected that the catalyst lifetime using the inventive process is at least three times longer due to the low SOR temperature. This will allow the increase of the average selectivity by at least +3%.

3.3 Example 3

Figure 5:
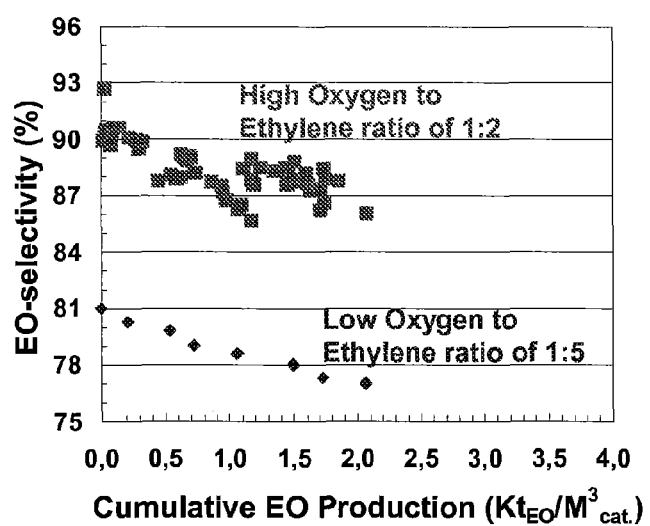
FIG. 5 shows the relationship between EO-selectivity (%) and cumulative EO production ($Kt_{EO}/M^3_{cat.}$) for catalyst 1 using a ratio of ethylene to oxygen of 2:1 and a ratio of ethylene to oxygen of 5:1.

Additional results of a second long term experiment are shown in FIG. 5.

Here Catalyst 1 was used. Comparison was made between catalyst performance using a ratio of ethylene to oxygen of 2:1 and catalyst performance using a ratio of ethylene to oxygen of 5:1.

The selectivity using a ratio of ethylene to oxygen of 2:1 is almost 10% higher.

| Ratio (ethylene:oxygen) | 5:1 | 2:1 |
|---|---|---|
| EO Selectivity (%) | 77-81 | 86-90 |
| Workrate ($Kg_{EO}/m^3_{cat}$/hr) | 250 | 750 |
| Ethylene (mole %) | 35 | 50 |
| Oxygen (mole-%) | 7 | 25 |
| Ethyl chloride (parts per million (ppm) by volume) | 2.7 | 2.7 |
| Nitrogen (mole-%) | — | 5 |
| Methane | balance | balance |
| Temperature (° C.) | 240– | 230– |
| GHSV ($hr^{-1}$) | 5000 | 16000 |
| Pressure (absolute) | 16 bars | 16 bars |

It is surprising that even using a highly active catalyst having an active composition as simple as silver and just one promoting element as cesium, gives a selectivity in the range of 85 to 91%.

In addition, a triple workrate could be achieved by an operation at a similar temperature. This will have a direct impact on the production capacity.

3.4 Example 4

0.50 g. of the catalyst 1 was loaded in a process microchannel to provide a catalyst bed length of 5.6 cm. The catalyst volume was 0.406 ml. The reactant composition contained:

| ethylene | 19 mole % |
|---|---|
| oxygen | 10 mole % |
| ethyl chloride | 2.7 parts per million (ppm) by volume |
| nitrogen | 5 mole % |
| methane | balance |

The GHSV for the flow of process fluid in the process microchannel was 22500 $hr^{-1}$. At a pressure of 16 bars (absolute) and a temperature of 235° C., a workrate of 750 $Kg_{EO}/m^3_{cat}$/hr was obtained with a selectivity to ethylene oxide of 89.1%.

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process, comprising:
    reacting ethylene and oxygen or a source of oxygen in the presence of a catalyst in a microchannel reactor to form a product comprising ethylene oxide,
    wherein the catalyst contains silver or silver compound and a support and the catalyst is in the form of particulate solids having a mean particle diameter from 1 to 1000 µm and
    wherein the molar ratio of oxygen to ethylene is from 1:2 to 1:1, wherein the gas hourly space velocity is from about 4 000 to 100 000 $h^{-1}$ and
    wherein ethylene oxide is produced at a rate of at least 250 kilograms of ethylene oxide per cubic meter of catalyst per hour and having a selectivity to ethylene oxide of at least 82%, maintaining an average temperature in the reaction zone below 250° C. and
    wherein the process takes place at a pressure from atmospheric to 100 atmospheres and
    wherein the microchannels have at least one internal dimension of height or width of up to 10 mm, and
    wherein the contact time of the process fluids with the catalyst within the reactor is in the range from 50 to 900 milliseconds (ms).

2. The process as claimed in claim 1, wherein the production run continues until at least 4 kilotons of ethylene oxide are produced per cubic meter of catalyst.

3. The process of claim 1, wherein the selectivity to ethylene oxide is in the range from about 85 to about 95%.

4. The process of claim 1, wherein the ethylene oxide is produced at a rate in the range from about 500 to about 5000 kilograms per cubic meter of catalyst per hour.

5. The process of claim 1, wherein the mean particle diameter of the catalyst is from 75 to 300 µm.

6. The process of claim 1, wherein the catalyst comprises one or more of Mo, Re, W, V, Nb, Sb, Sn, Pt, Pd, Cs, Zr, Cr, Mg, Mn, Cu, Ni, Co, Ce, Ti, Hf, Tl, Th, Ga, Ge, Zn, Rh, Ru, Fe, an oxide of one or more thereof, alkali or alkaline earth metal, sulfur or an oxide thereof, or a mixture of two or more thereof.

7. The process as claimed in claim 6, wherein the catalyst comprises silver, one or more alkali metal promoters, and optionally one or more co-promoters, wherein said co-promoters are sulfur, molybdenum, tungsten, chromium, rhenium or a mixture of two or more thereof.

8. The process of claim 1, wherein the catalyst is free of rhenium.

9. The process of claim 1, wherein the catalyst's active composition comprises silver and a promoting amount of cesium.

* * * * *